(12) United States Patent
Rutter et al.

(10) Patent No.: US 8,703,494 B2
(45) Date of Patent: Apr. 22, 2014

(54) SYSTEMS AND METHODS FOR DETERMINING THE PERCENTAGE OF GLYCATED HEMOGLOBIN

(75) Inventors: William J. Rutter, San Francisco, CA (US); Jang H. Han, Lafayette, CA (US); Taewoo Kwon, Burlingame, CA (US)

(73) Assignee: Relia Diagnostic Systems, LLC, San Francisco, CA (US)

( * ) Notice: Subject to any disclaimer, the term of this patent is extended or adjusted under 35 U.S.C. 154(b) by 521 days.

(21) Appl. No.: 12/784,280

(22) Filed: May 20, 2010

(65) Prior Publication Data

US 2011/0070658 A1    Mar. 24, 2011

Related U.S. Application Data

(60) Provisional application No. 61/180,075, filed on May 20, 2009.

(51) Int. Cl.
*G01N 33/72* (2006.01)
*C12M 1/34* (2006.01)
*G01N 33/52* (2006.01)

(52) U.S. Cl.
USPC ............... 436/67; 436/518; 436/522; 436/66; 436/161; 436/164; 436/172; 436/177; 435/7.1; 435/69.6; 435/286.7; 435/287.2; 435/288.7; 422/400; 422/417; 422/425; 422/427; 422/430; 422/70; 422/82.08

(58) Field of Classification Search
USPC .............. 435/7.1, 286.5, 287.2, 288.6, 288.7; 436/518, 522, 66, 67, 161, 164, 172, 436/177; 422/400, 417, 425, 427, 430, 422/82.08
See application file for complete search history.

(56) References Cited

U.S. PATENT DOCUMENTS 6,162,645 A * 12/2000 Lee et al. ................... 436/67
6,677,158 B2 * 1/2004 Hud et al. .................. 436/67
7,270,970 B2 * 9/2007 Anderson et al. ........... 435/7.94

* cited by examiner

*Primary Examiner* — Gail R Gabel
(74) *Attorney, Agent, or Firm* — Dennis A. Bennett; Suman R. Mirmira (57) ABSTRACT

Described herein are systems and methods for assaying a sample to quantitatively determine the percentage of glycated hemoglobin in the sample.

8 Claims, 8 Drawing Sheets

Examples of boronic acid derivatives

Amine group containing phenylboronic acid 3-aminophenyl boronic acid

4-Amino-3-nitrophenylboronic acid

Sulfhydryl group containing phenylboronic acid 3- mercaptophenylboronic acid 4- mercaptophenylboronic acid

Fig. 5a

Conjugation Reactions of Boronic Acid Derivatives

R is fluorophore, R'-NH₂ is boronic acid derivative having amine group like 3-aminophenyl boronic acid or 4-amino-3-nitrophenylboronic acid.

Example of boronic acid conjugate:

Fluorophore, DY-782 NHS-ester (Dyomics) labeled 3-aminophenylboronic acid by conjugation reaction

Fig. 5b

Conjugation Reactions of Boronic Acid Derivatives

R is fluorophore, R'-SH is boronic acid derivative having sulfhydryl group like 3-mercaptophenyl boronic acid or 4- mercaptophenylboronic acid.

Example of boronic acid conjugate:

Fluorophore, DY-636 Maleimide (Dyomics) labeled 3-mercaptophenylboronic acid

Fig. 6

Fluorophores Containing Boronic Acid Moiety

Dy-782 containing boronic acid moiety

Dy-636 containing boronic acid moiety

SYSTEMS AND METHODS FOR DETERMINING THE PERCENTAGE OF GLYCATED HEMOGLOBIN

This application claims the benefit of U.S. Provisional Application No. 61/180,075, entitled "Test Strips and Methods for Determining the Percentage of Glycated Hemoglobin," filed on May 20, 2009, the disclosure of which is incorporated herein by reference in its entirety.

BACKGROUND OF THE INVENTION

Diabetes mellitus is a chronic disorder characterized by insulin deficiency, hyperglycemia, and high risk for development of complications of the eyes, kidneys, peripheral nerves, heart and blood vessels. The disease is highly prevalent, affecting as many as 16 million people in the U.S. The disease is also expensive, in terms of both human suffering and dollars; it is estimated that approximately 1 in every 7 health care dollars spent in the U.S. goes to diabetes care, mostly for treatment of the chronic complications. In the U.S., diabetes is the most common cause of blindness in young adults, kidney failure, and non-traumatic limb amputation.

The Diabetes Control and Complications Trial (DCCT), completed in 1993, showed that the risk for development and progression of the chronic complications of diabetes is closely related to the degree of glycemic control, as measured by glycated hemoglobin (GHb) determinations. The DCCT also provided a large body of data relating GHb values to mean blood glucose. Thus, the DCCT results have set the stage for establishing specific diabetes treatment goals using GHb as an index of mean blood glucose concentration.

Ideally, early detection of altered blood glucose levels would lead to careful monitoring and long term control of blood glucose concentrations. There is a need for a rapid and accurate assay for measuring blood glucose levels. Many current blood glucose monitoring tests are subject to recent food intake or other lifestyle habits that may cause short term glucose levels to fluctuate dramatically. These may not give an accurate view of trends in blood glucose levels and may mask elevated baseline levels. As mentioned, it has previously been established that elevated blood glucose leads to increased glycation of hemoglobin (Hb) in circulating erythrocytes and that the level of glycated Hb is correlated with the glucose levels over about a three month period. Therefore, recent food intake has little impact on the glycated Hb level, thus giving a more accurate level of mean glucose levels in the blood.

A variety of diagnostic assays and related devices have been developed for point-of-care (POC) testing. In view of the convenience of POC diagnostic assays and related devices, the timeliness of their results, and the high incidence of diabetes, the need for an early diagnostic test for discovery of predilection to diabetes, and also for monitoring therapy has emphasized the extraordinary need for a POC diagnostic test. This is best accommodated in non hospital environments and also in situations where phlebotomists are not required (i.e., there is no need for blood draws). Generally, POC devices may be portable or otherwise transportable. In some cases, they may even be handheld.

Further, because there is a lot of variability in the tests that are currently available, it would be desirable to provide POC systems that have high sensitivity, precision, accuracy, and reliability of measurement, and yet are readily available to large populations. The present invention describes a method of determining blood glucose levels by measuring the amount of glycated hemoglobin in a small sample of blood making use of chromatographic test strips in an assay system that is amenable to POC device configuration.

SUMMARY

The present invention is based, in part, on the discovery of methodologies for the quantitative analysis of hemoglobin (Hb), glycated hemoglobin (GHb), and other variants to be tested. Accordingly the present invention provides systems for performing the assays and methods for determining the amount of glycated hemoglobin in a blood sample. In some embodiments, the systems and methods described here may be used in point-of-care (POC) testing, with devices that may be portable and even handheld, and in some cases may be battery-operated. In certain embodiments, the methodologies described here may be CLIA-waived (where "CLIA" refers to Clinical Laboratory Improvement Amendments).

In one aspect of the invention, it provides a glycated hemoglobin coupled to both an antibody that recognizes hemoglobin, labeled with a first detectable marker, and to a boronic acid, or a derivative thereof, labeled with a second detectable marker.

In another aspect of the invention, it provides a method for determining the percentage of glycated hemoglobin in a sample. In one embodiment, the method comprises detecting a first detectable marker coupled to a first agent that binds hemoglobin in the sample and a second detectable marker coupled to a second agent that binds only glycated hemoglobin in the sample and determining the percentage of glycated hemoglobin in the sample based on the amount of the first detectable marker and the second detectable marker detected in the sample. The signals from the first detectable marker and the second detectable marker may, optionally, be measured simultaneously.

In another embodiment, the method comprises detecting a first detectable marker coupled to a first agent that binds hemoglobin in the sample and a second detectable marker coupled to a second agent, a boronic acid or a derivative thereof, that binds only glycated hemoglobin in the sample and determining the percentage of glycated hemoglobin in the sample based on the amount of the first detectable marker and the second detectable marker detected in the sample. The signals from the first detectable marker and the second detectable marker may, optionally, be measured simultaneously.

In yet another embodiment, the method comprises the steps of contacting the hemoglobin released from cells in a sample with a first agent, labeled with a first detectable marker, that binds hemoglobin and with a second agent that is labeled with a second detectable marker, that binds only glycated hemoglobin; immobilizing the detectably labeled hemoglobin on a solid support; measuring signals from the first detectable marker and the second detectable marker immobilized on the solid support; and determining the percentage of glycated hemoglobin in the sample based on the signals from the first detectable marker and the second detectable marker. The signals from the first detectable marker and the second detectable marker may, optionally, be measured simultaneously.

In yet another embodiment, the method comprises the steps of contacting the hemoglobin released from cells in a sample with a first agent, labeled with a first detectable marker, that binds hemoglobin and with a second agent, a boronic acid or a derivative thereof, that is labeled with a second detectable marker, that binds only glycated hemoglobin; immobilizing the detectably labeled hemoglobin on a solid support; measuring signals from the first detectable marker and the second detectable marker immobilized on the solid support; and determining the percentage of glycated hemoglobin in the sample based on the signals from the first detectable marker and the second detectable marker. In an exemplary embodiment, signals from the first detectable marker and the second detectable marker are measured simultaneously.

In another embodiment, the method comprises the steps of contacting the hemoglobin released from cells in a sample with a first agent, labeled with a first detectable marker, that binds hemoglobin and with a second agent that is labeled with a second detectable marker, that binds only glycated hemoglobin; immobilizing the detectably labeled hemoglobin, including the detectably labeled glycated hemoglobin, at the same region on a solid support; simultaneously measuring signals from the first detectable marker and the second detectable marker immobilized on the solid support; and determining the percentage of glycated hemoglobin in the sample based on the signals from the first detectable marker and the second detectable marker. The first detectable marker is a first fluorophore that fluoresces upon exposure to light of a first wavelength and the second detectable marker is a second fluorophore that fluoresces upon exposure to light of a second wavelength and the signals from the first detectable marker and the second detectable marker immobilized on the solid support are measured by exposing the region of the solid support to which hemoglobin, including glycated hemoglobin, is immobilized to light of the first and second wavelengths.

In another aspect of the invention, it provides a system for quantitatively determining the percentage of glycated hemoglobin in a blood sample. In one embodiment, the invention provides a test strip for quantitatively determining the percentage of glycated hemoglobin in a blood sample. The test strip comprises a chromatographic strip; a coating on a portion of the chromatographic strip that comprises a capture agent that binds to hemoglobin in a sample; a region on the chromatographic strip to which sample is added; and a region on the chromatographic strip that comprises a first agent, labeled with a first detectable marker, that binds hemoglobin, and a second agent, labeled with a second detectable marker, that binds only glycated hemoglobin, wherein the region on the chromatographic strip that comprises the first agent and the second agent is located (i) at the region to which the sample is added or (ii) in between the region to which the sample is added and the region comprising the capture agent such that sample that is added to the test strip flows across the region comprising the first and second agents before reaching the region comprising the capture agent. Optionally, the first detectable marker is a fluorophore that fluoresces upon exposure to light of a first wavelength and the second detectable marker is a fluorophore that fluoresces upon exposure to light of a second wavelength. In an exemplary embodiment the first and second detectable markers are detected simultaneously.

In another embodiment, the test strip comprises a chromatographic strip; a coating on a portion of the chromatographic strip that comprises a capture agent that binds to hemoglobin in a sample; a region on the chromatographic strip to which sample is added; and a region on the chromatographic strip that comprises a first agent, labeled with a first detectable marker, that binds hemoglobin, and a second agent comprising a boronic acid or a derivative thereof, labeled with a second detectable marker, that binds only glycated hemoglobin, wherein the region on the chromatographic strip that comprises the first agent and the second agent is located (i) at the region to which the sample is added or (ii) in between the region to which the sample is added and the region comprising the capture agent such that sample that is added to the test strip flows across the region comprising the first and second agents before reaching the region comprising the capture agent.

BRIEF DESCRIPTION OF FIGURES

FIG. 1 shows an exemplary flow diagram for determination of % HbA1c in a blood sample. The blood sample is lysed to release Hb from red blood cells. The released Hb is contacted with an antibody, detectably labeled with a first fluorophore, that binds Hb (fl1-Ab1) and a boronic acid derivative, BD, detectably labeled with a second fluorophore, that binds only glycated Hb (fl2-BD). The labeled Hb and glycated Hb are exposed to predetermined wavelengths of light directed to the first and second fluorophores, respectively, to induce fluorescence. The percent of glycated Hb is determined based on the fluorescence from the first and second fluorophores.

FIG. 2 shows a schematic for determination of glycated Hb in a blood sample according to one embodiment of the invention. The blood sample is exposed to a lysis solution to liberate the Hb from the red blood cells. The lysed sample is added to a chromatographic strip that comprises an antibody, detectably labeled with a first fluorophore, that binds Hb (fl1-Ab1) and a boronic acid derivative, 3-aminophenylboronic acid (PB) detectably labeled with a second fluorophore, that binds only glycated Hb (fl2-PB). Hemoglobin from the sample binds the antibody labeled with the first fluorophore and glycated hemoglobin from the sample binds the boronic acid derivative, detectably labeled with the second fluorophore. The labeled hemoglobin flows along the chromatographic strip to a capture zone, detection area or "test band" comprising an anti-Hb antibody that binds to (and thus captures or immobilizes) hemoglobin. The chromatographic strip is exposed to light of 635 nm and 800 nm wavelengths to induce fluorescence from the first and second fluorophores. The percent of glycated Hb is determined based on the fluorescence from the first and second fluorophore.

FIG. 3 shows an alternative schematic for determination of glycated Hb in a blood sample according to another embodiment of the invention. The blood sample is exposed to a lysis solution to liberate the Hb from the red blood cells. The lysis solution comprises an antibody, detectably labeled with a first fluorophore, that binds Hb (fl1-Ab1) and a boronic acid derivative, 3-aminophenylboronic acid (PB) detectably labeled with a second fluorophore, that binds only glycated Hb (fl2-PB). Hemoglobin from the sample binds the antibody labeled with the first fluorophore and glycated hemoglobin from the sample binds the boronic acid derivative, detectably labeled with the second fluorophore. The labeled hemoglobin is added to a chromatographic strip and flows along the chromatographic strip to a capture zone, detection area or "test band" comprising an anti-Hb antibody that binds to (and thus captures or immobilizes) hemoglobin. The signals from the first detectable marker and the second detectable marker immobilized on the chromatographic strip are measured. The percent of glycated Hb is determined based on the signals from the first and second fluorophore.

FIG. 7 shows a schematic for an exemplary test strip of the invention. The test strip depicted is a bidirectional lateral flow test strip wherein fluid added at Port I located at or near End 1 flows towards End 2 and fluid added at Port II located at or near End 2 flows towards End 1. In the test strip shown, sample is added at Port I and flows towards the reaction regions or capture zones, or detection areas comprising a "test band" and two "control bands." The test band comprises a capture agent that binds to (and thus captures or immobilizes) the analyte in the sample, for example the test band may comprise anti-Hb antibody that binds to hemoglobin. The control bands, "high control" and "low control" comprise a capture agent that binds to, and thus capture, a control present in the sample. In alternate embodiments, the test strips of the invention may comprise none, one or more than two control bands. Fluid such as additional sample or buffer, e.g., wash buffer may optionally be added at Port II as shown.

DETAILED DESCRIPTION

Described herein are systems and methods for assaying a blood sample to quantitatively determine the percentage of glycated hemoglobin in the blood sample. Generally, the methods and systems described here may be used in a point-of-care (POC) device as well as other in vitro diagnostic (IVD) devices, as appropriate. In some embodiments, the POC systems are designed for on-site testing by non-technical personnel and may be CLIA waived. In certain cases, the methods and systems described here may be used in devices that are relatively inexpensive to manufacture, and thus may be made widely available. In addition, they may be used in devices, such as POC devices, that can provide quantitative analysis of the blood samples in a relatively short period of time (e.g., 60 minutes or less, 50 minutes or less, 40 minutes or less, 30 minutes or less, 20 minutes or less, 15 minutes or less, 10 minutes or less, or five to ten minutes, from the time of taking the sample). The systems and assay methods described herein can be used with devices such as those described in U.S. patent application Ser. No. 12/760,518, filed on Apr. 14, 2010 and entitled "Diagnostic Devices and Related Methods," which is incorporated herein by reference in its entirety.

Hemoglobin is the oxygen-carrying pigment that gives blood its red color and also the predominant protein in red blood cells. About 90% of hemoglobin is hemoglobin A (the "A" stands for adult type). Although one chemical component accounts for 92% of hemoglobin A, approximately 8% of hemoglobin A is made up of minor components that are chemically slightly different. These minor components include hemoglobin A1c, A1b, A1a1, and A1a2. Hemoglobin A1c (HbA1c) is a minor component of hemoglobin to which glucose is bound. HbA1c also is referred to as glycosylated hemoglobin, glucosylated hemoglobin or glycated hemoglobin (GHb). These terms for GHb are used interchangeably herein.

As used herein, "hemoglobin" (Hb) refers to all components of hemoglobin or "total" hemoglobin, including glycated hemoglobin. Accordingly an agent that binds, captures or immobilizes hemoglobin also binds, captures or immobilizes glycated hemoglobin.

In one aspect of the invention, the invention provides a method for determining the percentage of glycated hemoglobin in a sample. In one embodiment, the method comprises detecting a first detectable marker coupled to a first agent that binds hemoglobin in the sample and detecting a second detectable marker coupled to a second agent that binds only glycated hemoglobin in the sample. The percentage of glycated hemoglobin in the sample can be determined based on the amount of the first detectable marker and the second detectable marker detected in the sample.

The sample can be any fluid that comprises hemoglobin. In one embodiment, the sample is a blood sample, i.e., a drop or other required quantity of blood. In another embodiment, the sample comprises cells, e.g., red blood cells ("RBCs"), containing hemoglobin isolated from blood. The cells may, but need not be lysed or made permeable to release the hemoglobin.

In one embodiment, the sample is a blood sample or a sample comprising cells containing hemoglobin isolated from blood and the blood or the blood cells are lysed or made permeable in order to release hemoglobin from the cells. The sample can be contacted with a lysing agent or agents that make the cells permeable for sufficient time to release the hemoglobin. Any other lysing means or means to make permeable known to one of skill in the art may be also used. In one embodiment, a lysis buffer may be used. For example, the blood sample may be lysed by in a 4 mM phosphate buffer, pH 7.5, 1% Triton X-100, 150 mM NaCl, for 1-2 minutes, or other lysis buffers known to one of skill in the art. In another embodiment, mechanical means, for example, high-energy ultrasound (or "sonnication") may be used.

The lysed sample comprising hemoglobin released from the RBCs can then be contacted with the first agent, labeled with a first detectable marker, that binds hemoglobin and a second agent, labeled with a second detectable marker, that binds only the glycated hemoglobin ("GHb") fraction of hemoglobin. The first agent binds hemoglobin forming a first detectable complex. The second agent binds GHb. Thus, as shown, for example, in FIGS. 2 and 3, glycated hemoglobin has two (2) labels, one from the agent that binds hemoglobin and one from the agent that is specific for glycated hemoglobin. The first detectable marker and the second detectable marker can be detected and the percentage of glycated hemoglobin in the sample can be determined based on the amount of the first detectable marker and the second detectable marker detected in the sample.

In one embodiment, any first agent that is not bound to hemoglobin and any second agent not bound to glycated hemoglobin is separated from the first agent and the second agent that is bound to hemoglobin and glycated hemoglobin, respectively, before the first and second detectable markers are detected. Such separation can be performed by any means now known or later discovered, including, but not limited to, placing the sample in an electric field, via electrophoresis, e.g., gel or capillary electrophoresis, or by immobilizing the hemoglobin.

In one embodiment of the invention, the hemoglobin released from cells in a blood sample is contacted with a first agent, labeled with a first detectable marker, that binds hemoglobin and with a second agent, boronic acid or a derivative thereof, that is labeled with a second detectable marker, that binds only glycated hemoglobin. The detectably labeled hemoglobin, including the detectably labeled glycated hemoglobin, is then localized in a detection area from which signals from the first and second detectable markers are measured. In one embodiment, the hemoglobin, including the glycated hemoglobin, is localized in the same detection area from which signals from the first and second detectable markers are measured. In another embodiment, the glycated hemoglobin is localized in a detection area, e.g., a first detection area, from which signals from the first and second detectable markers are measured and unglycated hemoglobin is localized in a different detection area, e.g., a second detection area, from which the signal from only the first detectable marker is measured.

Any means of localization known to one of skill in the art can be used. For example, the detectably labeled hemoglobin can be immobilized on a solid support. Any solid support to which a protein can be immobilized can be used to immobilize the detectably labeled hemoglobin. Exemplary solid supports include, but are not limited to, a chromatographic strip, e.g., a lateral flow test strip, a dipstick, a microfluidic device, glass or plastic beads, plates or columns, magnetic beads with, or without, a glass or plastic coating etc. Other solid supports, known to one of skill in the art, can also be used to immobilize the detectably labeled hemoglobin. In one embodiment, the solid support is a chromatographic strip, e.g., a lateral flow test strip, or a dipstick. In another embodiment, the solid support is a microfluidic device, a multi-well plastic plate used in ELISA assays, or a microcapillary system.

The solid support may, but need not, comprise an immobilized capture agent that binds to, and thereby immobilizes the hemoglobin. In one embodiment, the capture agent is immobilized on the support prior to contacting the sample or detectably labeled hemoglobin with the solid support. In another embodiment, the capture agent can be added to the sample (or present in a fluid, e.g., lysis buffer to which sample is added) before the sample is added to the solid support. The capture agent binds hemoglobin in the sample or other fluid to which sample is added. When sample is added to the solid support, e.g., a column comprising beads such as resin beads or biotin/streptavidin, the capture agent attaches to the support and thus immobilizes the bound hemoglobin. The term "capture agent," as used herein refers to a moiety (or composition) that can be immobilized on a solid support and that recognizes and binds hemoglobin in the sample, such that when it binds the hemoglobin, the hemoglobin is "captured" on the solid support.

The signals from the first detectable marker bound to hemoglobin and the second detectable marker bound to glycated hemoglobin can be measured by any means known to one of skill in the art. The signals from the first and second detectable markers can, but need not, be measured simultaneously. It is appreciated that when Hb, including GHb are immobilized on a solid support, only the signals from the detectably labeled agents bound or immobilized on the solid support, and not those free in solution are measured. In some embodiments, a wash step may be needed to eliminate any unbound detectably labeled agents. Means for ensuring that only the signals from the detectably labeled agents bound to hemoglobin and glycated hemoglobin are measured in those embodiments that use other separation techniques disclosed above will be apparent to one of skill in the art.

The percentage of glycated hemoglobin in the blood sample can be determined based on the signals from the first detectable marker and the second detectable marker. Further, the diabetic index may be determined according to the National Glycohemoglobin Standardization Program (NGSP).

Although the methods of the invention can be used with any system, as described above, that can be configured to quantitatively determine the percentage of glycated hemoglobin in a sample, the methods discussed herein are with reference to an exemplary system, a test strip comprising a chromatographic strip.

In one embodiment, hemoglobin released from cells in a sample, e.g., a blood sample, is contacted with the first agent, labeled with the first detectable marker, that binds hemoglobin, and the second agent, labeled with the second detectable marker, that binds only glycated hemoglobin, before the sample is added to the chromatographic strip. In one example, the cells in the sample may be lysed by contacting the sample with a lysis solution. The first and second detectably labeled agents, may, for example be present in the lysis solution, such that the Hb, once released from the lysed RBCs, is in contact with the first and second detectably labeled agents.

Alternatively, the sample is first subject to lysis and the lysed sample is subsequently contacted with the first and second detectably labeled agents. After the first and second detectably labeled agents have bound the hemoglobin and glycated hemoglobin, respectively, the sample is added to the chromatographic strip, where the hemoglobin (including the glycated hemoglobin) is immobilized by the capture agent and quantitatively detected.

Figure 1:
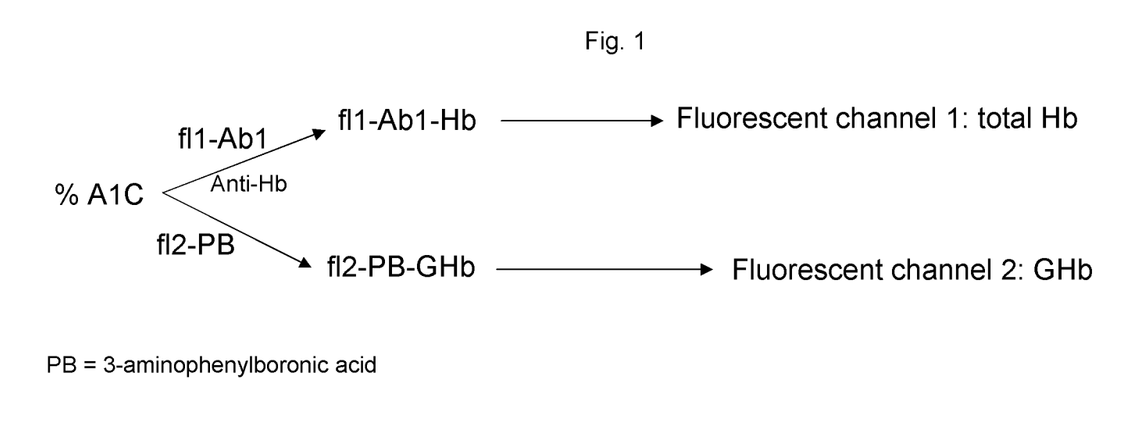
Figure 2:
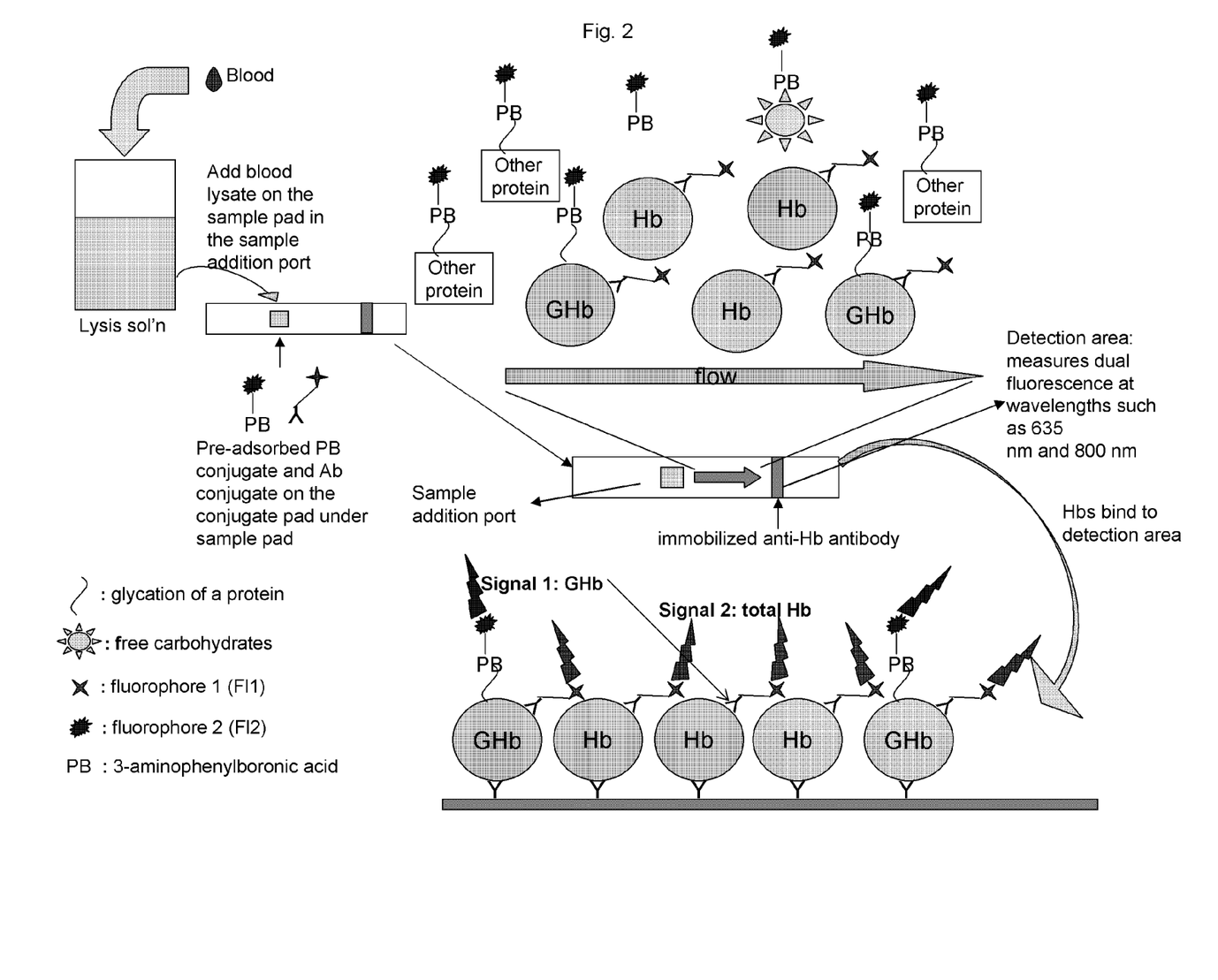
Figure 3:
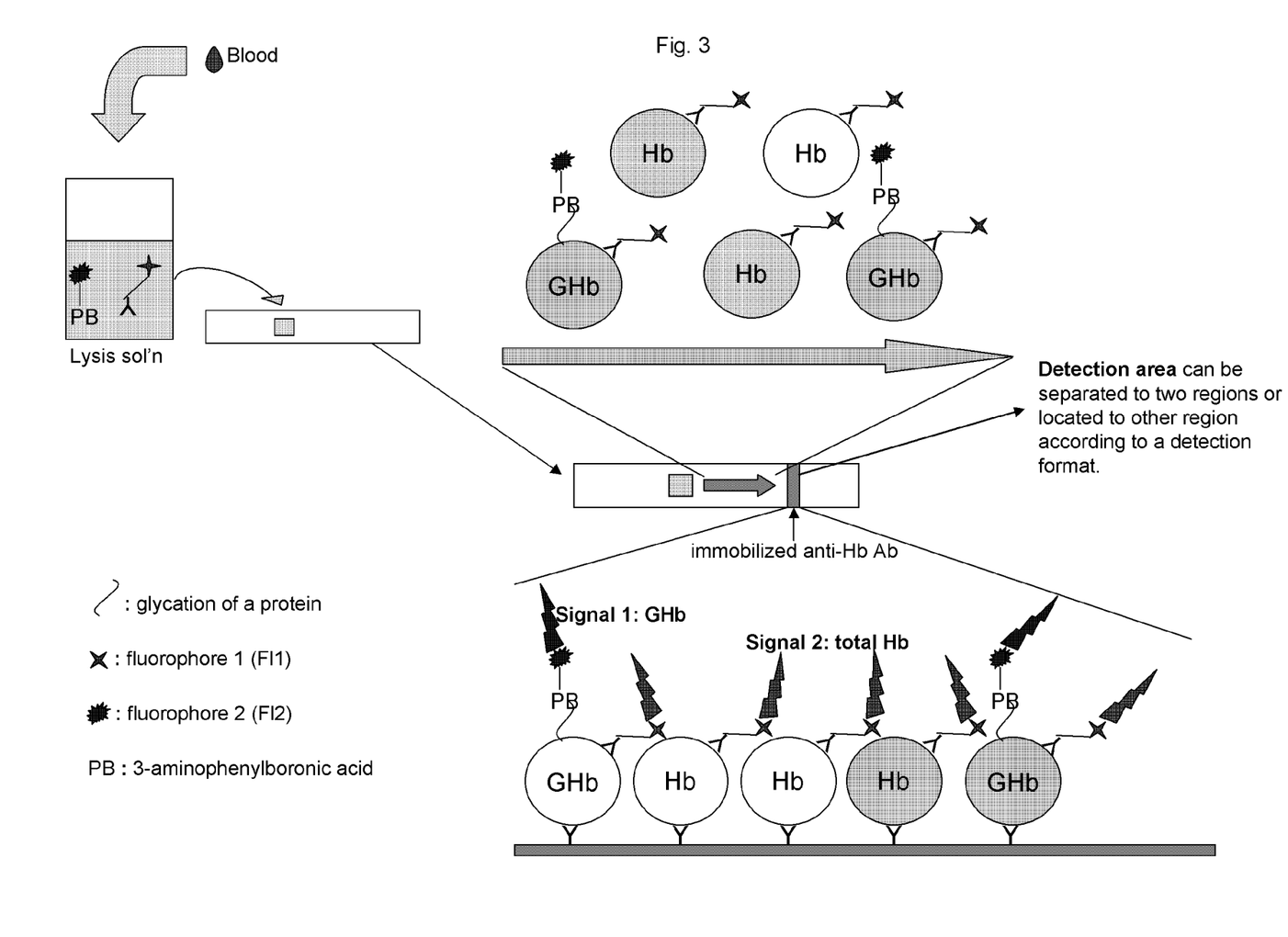

In another embodiment, as shown in FIG. 2, the lysed sample is added to the chromatographic strip without prior contact with the first and second detectably labeled agents. In this embodiment, the first and second detectably labeled agents are provided on the chromatographic strip at, or near, the point at which the lysed sample is added to the chromatographic strip such that the Hb and GHb in the lysed sample interact with the first and second detectably labeled agents on the chromatographic strip before flowing across the chromatographic strip to the portion comprising the capture agent.

Exemplary capture agents include, but are not limited to, an antibody, an antibody fragment, an antigen, a peptide, a hapten, or an engineered protein. In one embodiment, the capture agent is an antibody that recognizes and binds to Hb. The capture agent may be a monoclonal antibody or a polyclonal antibody, e.g., a polyclonal antibody recognizing common epitopes present in all hemoglobin molecules such as A, A2, F, C, D, E and S. Alternatively, the capture agent can comprise a mixture of antibodies specific for each variant. Further examples of capture agents include antibody fragments such as Fab, F(ab)2, nanobodies, diabodies, aptamers, adnectins, anticalins or a variety of other Hb-specific binding molecules derived by a variety of processes including DARPins and DARTs.

The first and second agents that binds hemoglobin and glycated hemoglobin respectively, can be any moiety or composition that bind hemoglobin and glycated hemoglobin respectively, and can be detectably labeled. In one embodiment, the first and second agents are an antibody or an antibody fragment, as discussed above. They may be monoclonal antibodies or polyclonal antibodies. It is noted that although the capture agent and the first agent both bind Hb, they neither bind the same epitope on Hb, nor do they compete with each other for binding to Hb.

Figure 4:
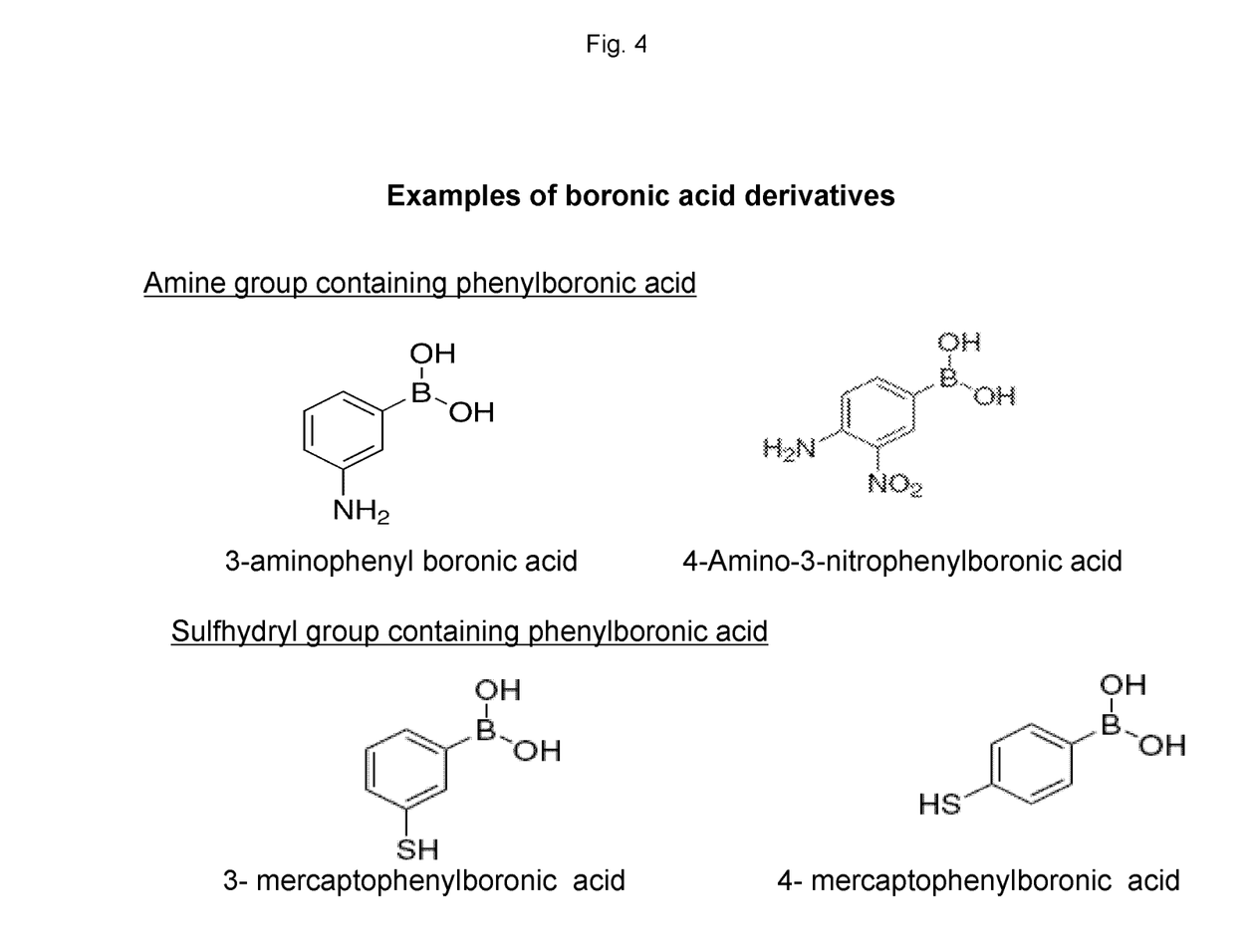
FIG. 4 shows exemplary boronic acid derivatives that can be coupled with a detectable marker to make a detectably labeled agent that binds glycated Hb.

In one embodiment, the second agent that binds glycated hemoglobin is a boronic acid [$RB(OH)_2$] or a derivative thereof. Any derivative of boronic acid now known, or later discovered, that specifically binds GHb can be used. Preferably the boronic acid derivative has high affinity for GHb as well as a high association rate (or "on-rate") for binding to GHb and a slow dissociation or "off" rate. Practical considerations, for example the ability or ease of coupling the boronic acid to the detectable marker, may favor the use of particular boronic acids. Such considerations are within the scope of one of skill in the art. The second agent, may, for example, be a phenyl boronate. Examples of boronic acid derivatives include, but are not limited to, 3-aminophenyl boronic acid, 4-amino-3-nitrophenylboronic acid, or 3-, or 4-sulfydryl (or mercapto) phenylboronic acid as well as those listed in Table 1 below. Chemical structures of exemplary boronic acid derivatives that can be used as the second agent for specifically binding GHb are shown in FIG. 4.

TABLE 1

Exemplary Boronic Acids and their Ionization constant ($pK_a$)

| Boronic acid, $RB(OH)_2$ | $pK_a$ |
|---|---|
| Boric acid | 9.0 |
| Methylboronic acid | 10.4 |
| Phenylboronic acid | 8.9 |
| 3,5-Dichlorophenylboronic acid | 7.4 |
| 3,5-Bis(trifluoromethyl)phenylboronic acid | 7.2 |
| 3-Methoxyphenylboronic acid | 8.7 |
| 4-Methoxyphenylboronic acid | 9.3 |
| 4-Carboxyphenylboronic acid | 8.4 |
| 2-Nitrophenylboronic acid | 9.2 |
| 4-Nitrophenylboronic acid | 7.1 |
| 4-Bromophenylboronic acid | 8.6 |
| 4-Fluorophenylboronic acid | 9.1 |
| 2-Methylphenylboronic acid | 9.7 |
| 3-Methylphenylboronic acid | 9.0 |
| 4-Methylphenylboronic acid | 9.3 |
| 3,5-Dimethylphenylboronic acid | 9.1 |
| 3-Methoxycarbonyl-5-nitrophenylboronic acid | 6.9 |
| 3-Pyridylboronic acid | 4.0, 8.2 |
| 8-Quinolinylboronic acid | 4.0, 10 |
| 2-($R^1R^2NCH_2$)phenylboronic acid | 5.2-5.8 |

The first and second detectable markers attached to the first and second agents, respectively, may be selected from a wide variety of materials. In embodiments where the first and second detectable markers are detected simultaneously or from the same region of, e.g., a solid support, it is appreciated that the first detectable marker is either different from the second detectable marker or at least, that the markers can be differentiated when detected. Examples of detectable markers include, but are not limited to particles, luminescent labels; calorimetric labels, fluorescent labels; chemical labels; enzymes; radioactive labels; or radio frequency labels; metal colloids; and chemiluminescent labels.

Detection methods based on absorption, change (or a lack of change) in color, optical methods, such as measuring light scattering, fluorescence, reflectance, luminescence (e.g., chemiluminescence), or electrical conductivity or capacitance, radioactivity (measured with a Geiger counter, etc.), electrochemical detection of released electroactive agents, such as indium, bismuth, gallium or tellurium ions, as described by Hayes et al. (Analytical Chem. 66:1860-1865 (1994)) or ferrocyanide as suggested by Roberts and Durst (Analytical Chem. 67:482-491 (1995)) may be employed. Other methods may also be used, as appropriate. Moreover, a single detection method may be used, or multiple (e.g., two, three) different detection methods may be used together.

In one embodiment, signals from the first detectable marker and/or the second detectable marker are measured by applying light from a first light source and/or a second light source to that region of the chromatographic strip where the total hemoglobin is immobilized. One or both of these light sources may comprise lasers. It is appreciated that the light sources can be of fixed or adjustable wavelengths and can be calibrated to deliver the frequency of light needed for optimum illumination of the first detectable marker and the second detectable marker. In an exemplary embodiment, the first or second detectably labeled agent can be exposed to red or infra-red light to induce fluorescence from the first and second detectable markers.

In one embodiment, the first or the second detectable markers may be a fluorophore which fluoresces at a wavelength that differs from that at which heme naturally fluoresces. In another embodiment, the first and the second detectable markers may be fluorophores which fluoresce at different wavelengths, and which are both different from that at which heme naturally fluoresces. In yet another embodiment, the signals from the first detectable marker and the second detectable marker are measured simultaneously. For example, the first and the second detectable markers that are detected simultaneously may be fluorophores which fluoresce at different wavelengths, and which are both different from that at which heme naturally fluoresces. In an exemplary embodiment, the first and the second detectable markers can be simultaneously exposed to red or infra-red light to induce fluorescence from the first and second detectable markers.

Examples of fluorophores that can be used include, but are not limited to, Dyomics, Dy-636 or Anaspec, HiLytePlus 647, both of which fluoresce at about 635 nm, or Dyomics, Dy-782 or Pierce, DyLight 800, both of which fluoresce at about 800 nm. Methods for the detection of two (or more) different detectable markers, e.g., fluorophores, as well as systems/devices that can be used for the detection are further described in U.S. patent application Ser. No. 12/760,518, filed on Apr. 14, 2010 and entitled "Diagnostic Devices and Related Methods," which was previously incorporated herein by reference in its entirety.

Figure 5A:
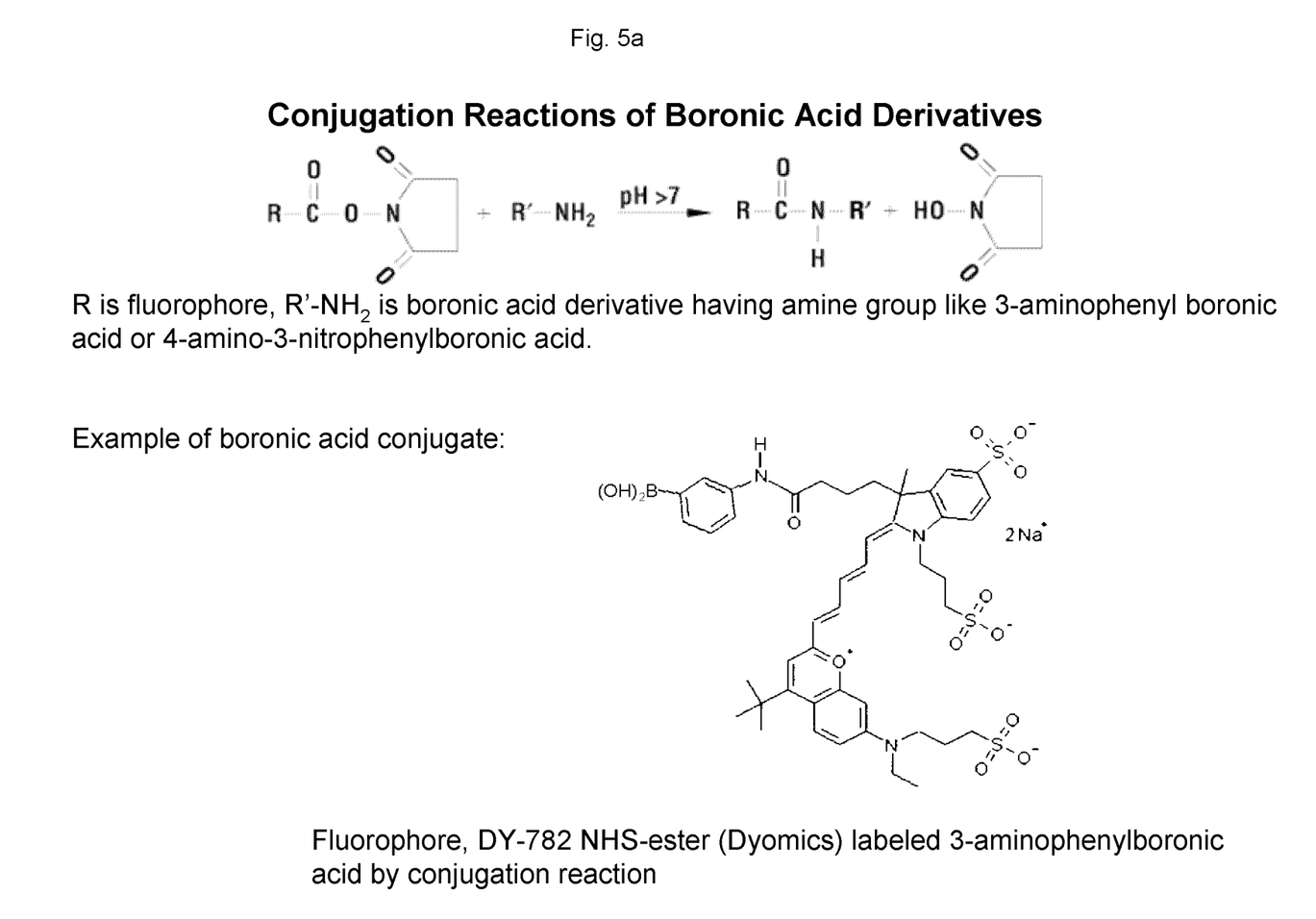
FIG. 5a shows the conjugation of a boronic acid containing amine residue at 3' position to a fluorophore, DY-782.
Figure 5B:
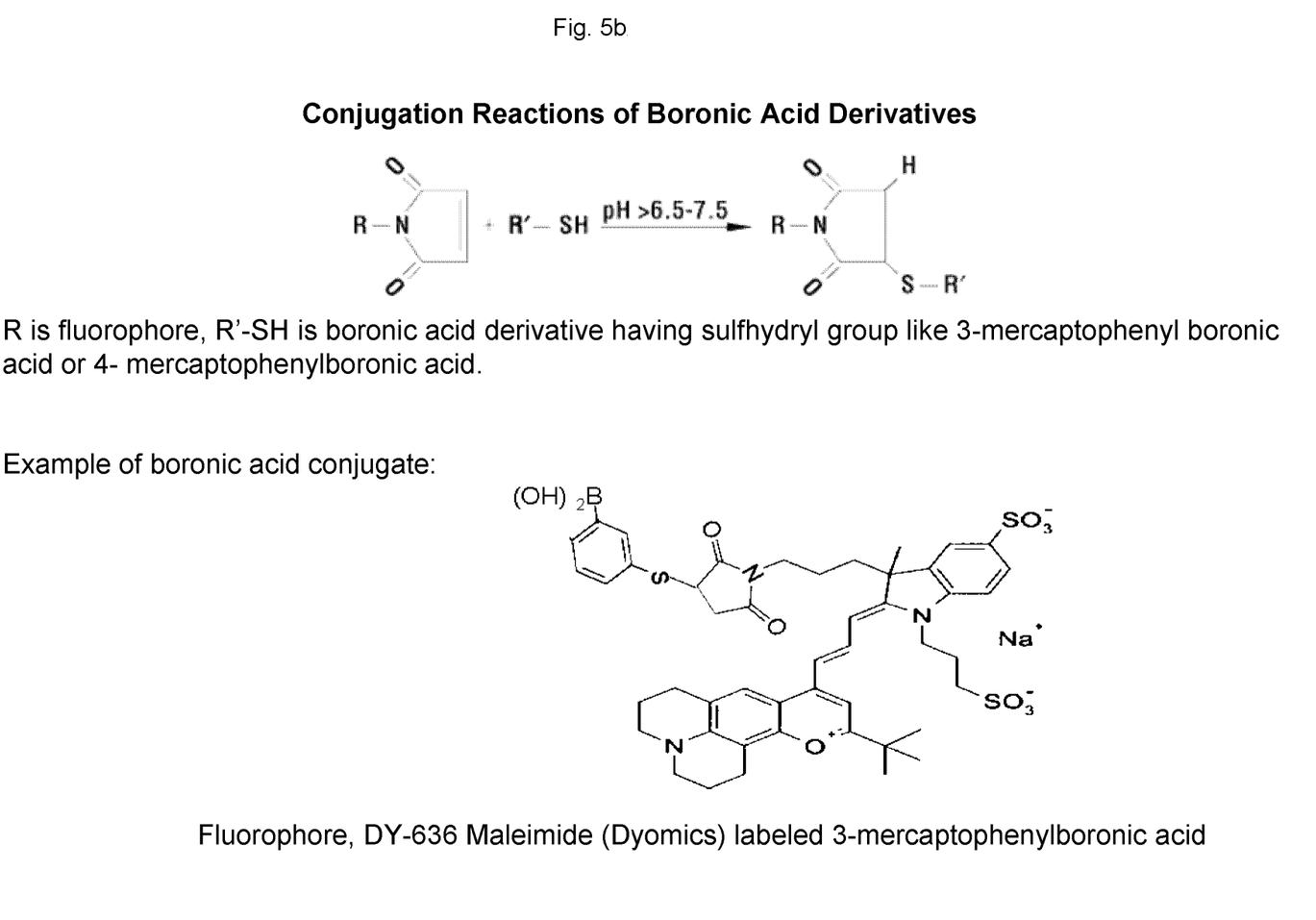
FIG. 5b shows the conjugation of a boronic acid containing sulfhydryl residue at 3' position to a fluorophore, DY-636.
Figure 6:
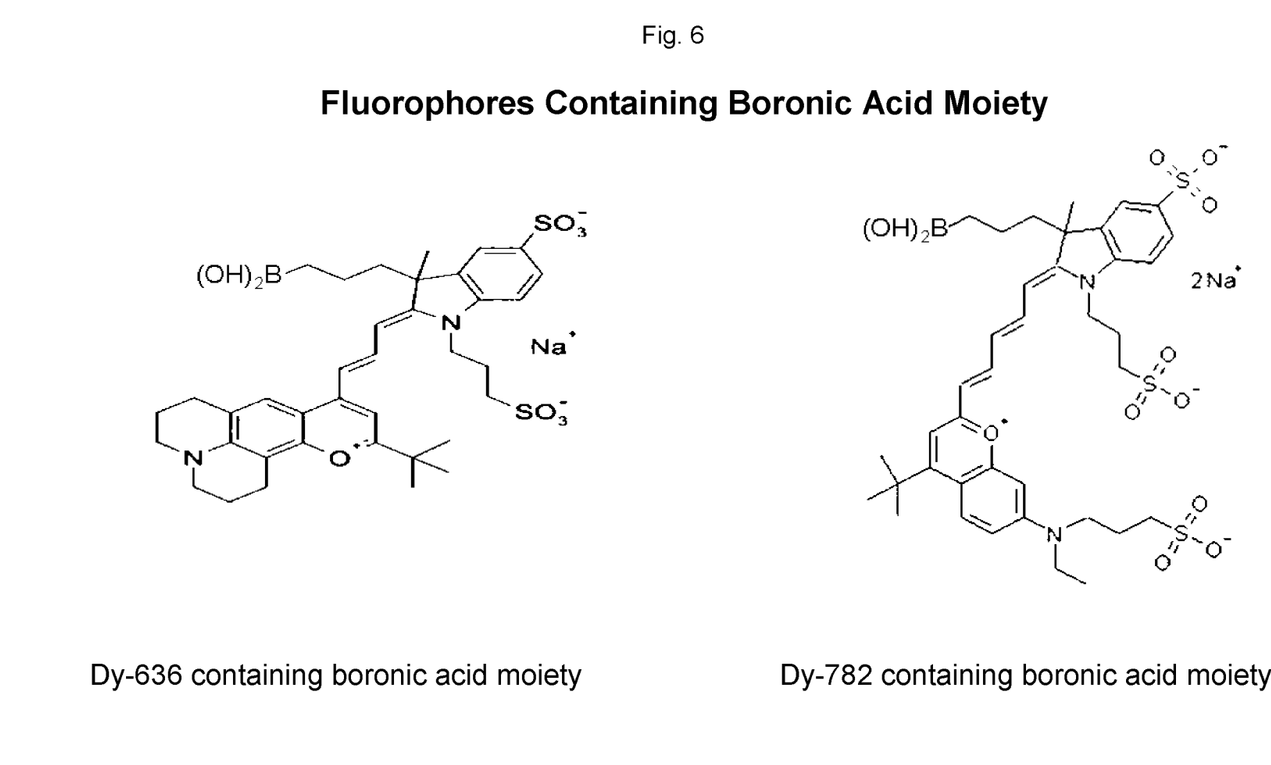
FIG. 6 shows the direct conversion or replacement of the carboxylic acid of a fluorophore with a boronic acid group without the use of an amine or a sulfhydryl group.
Figure 7:
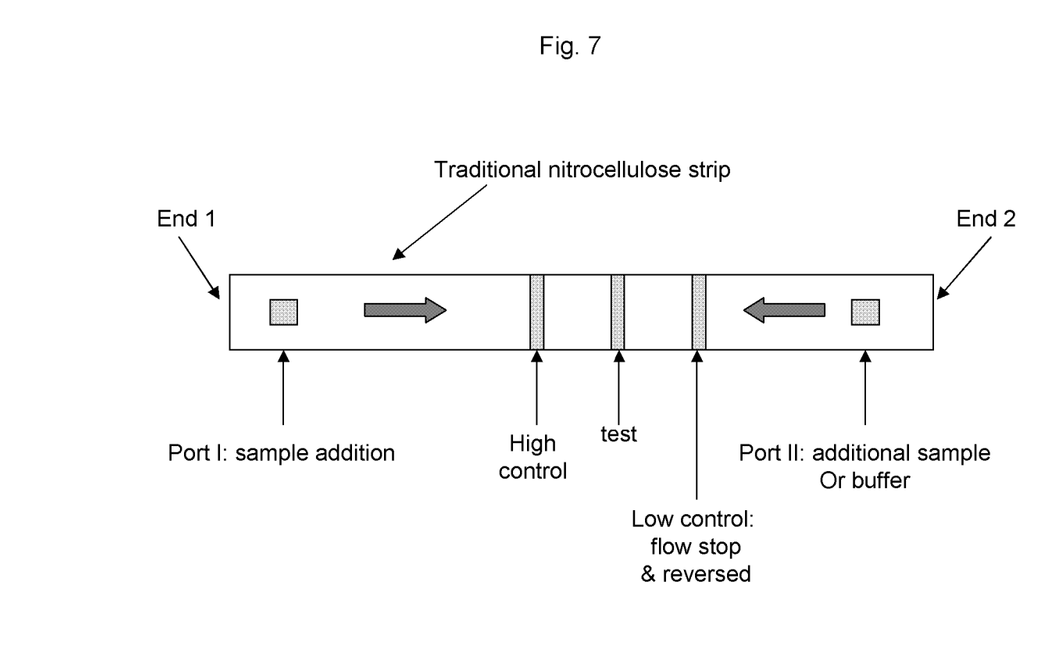

FIGS. 5a, 5b and 6 show exemplary reactions for the conjugation of a fluorophore to a boronic acid derivative that binds GHb. As shown in FIG. 5a, boronic acid containing an amine residue at 3' position (3-aminophenyl boronic acid) or at 4' position (4-Amino-3-nitrophenylboronic acid) can be conjugated to a fluorophore (e.g., DY-782) to form a fluorophore-boronic acid derivative conjugate with an amide link. FIG. 5b shows the conjugation of a boronic acid containing a sulfhydryl residue at 3' or 4' position (e.g., 3-mercaptophenyl boronic acid or 4-mercaptophenylboronic acid) to a fluorophore (e.g., DY-636). FIG. 6 shows the direct conversion or replacement of the carboxylic acid of a fluorophore with a boronic acid group without the use of an amine or a sulfhydryl group.

In an exemplary embodiment, the hemoglobin is released from cells in a sample and is contacted with a first agent, labeled with a first detectable marker, that binds hemoglobin and with a second agent that is labeled with a second detectable marker, that binds only glycated hemoglobin. The first detectable marker is a first fluorophore that fluoresces upon exposure to light of a first wavelength and the second detectable marker is a second fluorophore that fluoresces upon exposure to light of a second wavelength. The detectably labeled hemoglobin, including the detectably labeled glycated hemoglobin, is then immobilized at the same region on a solid support. The signals from the first detectable marker and the second detectable marker immobilized on the solid support are measured by exposing the region of the chromatographic strip to which hemoglobin, including glycated hemoglobin, is immobilized to light of the first and second wavelengths. The percentage of glycated hemoglobin in the sample is determined based on the signals from the first detectable marker and the second detectable marker. Optionally, the signals from the first detectable marker and the second detectable marker are measured simultaneously by simultaneously exposing the region of the solid support to which hemoglobin, including glycated hemoglobin, is immobilized to light of the first and second wavelengths.

In another aspect of the invention, the invention provides a glycated hemoglobin coupled to both an antibody that recognizes hemoglobin labeled with a first detectable marker and to a boronic acid or a derivative thereof labeled with a second detectable marker. In one embodiment, the boronic acid or derivative thereof is directly coupled to the detectable marker and can be detected by any means described above without the use of another agent, e.g., an antibody specific for either the boronic acid/boronic acid derivative or the bound GHb. The first and second detectable markers may be selected from any of the categories and examples of markers discussed above. Similarly the boronic acid, or derivative thereof, may be any suitable compound, for example, any of those described above.

In yet another aspect of the invention, the invention provides a system for quantitatively determining the percentage of glycated hemoglobin in a blood sample. The system can be any device that allows hemoglobin and glycated hemoglobin to be localized such that the relative quantities of the two can be determined. In one embodiment the system may be a test strip, e.g., a lateral flow test strip that supports uni-directional or bi-directional the flow of fluid across the test strip. Alternatively, the system is a dipstick that is dipped into the sample comprising hemoglobin released from RBCs. In the dipstick embodiment, it would be appreciated that the lysed sample is pre-mixed with the first and second detectably labeled agents. In another embodiment, the solid support is a multi-well plastic plate used in ELISA assays, or a microcapillary system.

In yet another embodiment, the system may be a microfluidics device. As an example, microfluidics devices may employ chambers in which the capture agent that binds total Hb is immobilized. Microfluidics methods and devices are described, for example, in Martinez et al., "Three-Dimensional Microfluidic Devices Fabricated in Layered Paper and Tape," PNAS, Vol. 105, No. 50 (Dec. 16, 2008) 19606-19611; P. K. Sorger, "Microfluidics Closes in on Point-of-Care Assays," Nature Biotechnology, Vol. 26, No. 12 (December 2008) 1345-1378; and B. Grant, "The 3 Cent Microfluidics Chip," The Scientist (Dec. 8, 2008), all of which are incorporated herein by reference in their entirety.

In one embodiment, the system is a test strip. The test strip comprises a chromatographic strip, a coating on a portion of the chromatographic strip that comprises an immobilized capture agent that binds to hemoglobin in a sample, a region on the chromatographic strip to which sample is added; and a region on the chromatographic strip that comprises a first agent, labeled with a first detectable marker, that binds hemoglobin, and a second agent, labeled with a second detectable marker, that binds only glycated hemoglobin. The test strip is configured such that sample that is added to the test strip flows across the region comprising the first and second detectably labeled agents before reaching the region that comprises the capture agent. For example, the region on the chromatographic strip that comprises the first detectably labeled agent and the second detectably labeled agent can be located either at the region to which the sample is added or in between the region to which the sample is added and the region comprising the capture agent. The first and second agents, the capture agent as well as the first and second detectable markers may be any agent or marker as previously described.

In one embodiment, the capture agent is immobilized in a capture zone. The capture zone may be made of any size or shape. It could be a band (e.g., a "test band"), i.e., in the shape of a rectangle that spans the width, partially or completely, of the test strip in a direction perpendicular to the flow of the fluid, or it could be a "spot" that is approximately circular or oval. The chromatographic strip may comprise more than one capture zone that capture hemoglobin, including glycated hemoglobin such that glycated and unglycated hemoglobin are co-localized.

In another embodiment, the chromatographic strip comprises at least two capture zones, a first capture zone comprising a first capture agent that immobilizes glycated hemoglobin and a second capture zone comprising a second capture agent that immobilizes unglycated hemoglobin. In this embodiment, the signal from the first detectable marker bound to hemoglobin would be measured from both the first and the second capture zones, whereas the signal from the second detectable marker bound only to glycated hemoglobin would be measured only from the first capture zone.

It must be appreciated that in light of the teachings herein, alternate embodiments of the methods and test strips can be contemplated. For example, a method in which hemoglobin released from RBCs is contacted with a detectably-labeled agent that specifically binds hemoglobin (e.g., an antibody) and then immobilized on a test strip that comprises two capture zones, a first capture zone with a capture agent specific for glycated hemoglobin (such as an anti-GHb antibody or a boronic acid or a derivative thereof), and a second capture zone that binds Hb, such that the sample is contacted with the first capture zone before it is contacted with the second capture zone is also within the scope of the invention. In this embodiment, the percentage of glycated hemoglobin in the sample can be determined based on the signals measured from the different positions of the test strip. Similarly, alternate embodiments of the test strip that comprise two capture zones, a first capture zone comprising a first capture agent that binds and immobilizes GHb that is located closer to the region of the test strip to which sample is added as compared to a second capture zone comprising a second capture agent that binds and immobilizes Hb is also within the scope of the invention.

In some embodiments, the test strip comprises a conjugate pad that comprises the first and second detectably labeled agents. Alternatively, or, in addition, the test strip may comprise a sample pad to which the sample is added. In embodiments of the test strip comprising both a conjugate pad and a sample pad, the sample pad may be located generally above the conjugate pad such that sample that is added to the sample pad flows to the conjugate pad and from the conjugate pad onto the chromatographic strip. Alternatively, the conjugate pad may be located on the chromatographic strip in between the sample pad and the region(s) comprising the immobilized capture agent (the capture zone(s)).

In one embodiment the sample pad acts like a reservoir and allows fluid, e.g., the sample or buffer, to be released slowly and constantly on to the conjugate pad and the chromatographic strip. This not only ensures even flow of sample across the test strip, but also provides sufficient time for the hemoglobin and glycated hemoglobin present in the sample to bind to the first and second detectably labeled agents, respectively, that are present in the conjugate pad. As will be appreciated, the retention time of the sample pad varies according to the size of the sample pad, the size of the test strip and the volume of sample added to the sample pad. In some embodiments, the sample pad can release the sample over a period of about 60 minutes, about 50 minutes, about 40 minutes, about 35 minutes, about 30 minutes, about 25 minutes, about 20 minutes, about 15 minutes, about 10 minutes, about 5 minutes, about 3 minutes, about 2 minutes, or about 1 minute. In an exemplary embodiment, the sample pad can hold and release buffer and sample for more than 20 minutes.

Exemplary configurations of test strips and systems that can be used to perform the methods/assays of the invention are further discussed in U.S. patent application Ser. No. 12/760,320, U.S. patent application Ser. No. 12/760,518, U.S. Pat. Nos. 6,528,323, 7,229,839, and 7,309,611, all of which are incorporated herein by reference in their entirety.

It must be appreciated that in light of the teachings herein, alternate embodiments of the methods and test strips can be contemplated. For example, a method in which hemoglobin released from RBCs is contacted with a detectably-labeled agent that specifically binds hemoglobin (e.g., an anti-Hb antibody) and then immobilized on a test strip that comprises two capture zones, a first capture zone with a capture agent specific for glycated hemoglobin (such as an anti-GHb antibody or a boronic acid or a derivative thereof), and a second capture zone that binds Hb, such that the sample is contacted with the first capture zone before it is contacted with the second capture zone is also within the scope of the invention. In this embodiment, the percentage of glycated hemoglobin in the sample can be determined based on the signals measured from the different positions of the test strip. Similarly, alternate embodiments of the test strip that comprise two capture zones, a first capture zone comprising a first capture agent that binds and immobilizes GHb that is located closer to the region of the test strip to which sample is added as compared to a second capture zone comprising a second capture agent that binds and immobilizes Hb is also within the scope of the invention.

While the test strips/systems and methods have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the appended claims.

What is claimed is:

1. A glycated hemoglobin coupled to both (i) an antibody that recognizes hemoglobin labeled with a first detectable marker and (ii) boronic acid, or a derivative thereof, wherein the boronic acid, or the derivative thereof, is labeled with a second detectable marker.

2. A test strip comprising:
   a chromatographic strip;
   a coating on a portion of the chromatographic strip, the coating comprising a capture agent that binds to hemoglobin in a sample;
   a region on the chromatographic strip to which sample is added; and
   a region on the chromatographic strip that comprises a first agent that binds hemoglobin and a second agent that binds only glycated hemoglobin, wherein the first agent is labeled with a first detectable marker and the second agent is labeled with a second detectable marker, wherein the capture agent and the first agent do not compete with each other for binding to hemoglobin, and wherein the region on the chromatographic strip that comprises the first agent and the second agent is located (i) at the region to which the sample is added or (ii) in between the region to which the sample is added and the region comprising the capture agent such that sample that is added to the test strip flows across the region comprising the first and second agents before reaching the region comprising the capture agent.

3. The test strip of claim 2, wherein the chromatographic strip comprises a conjugate pad that comprises the first agent labeled with the first detectable marker and the second agent labeled with the second detectable marker and wherein the conjugate pad is located (i) at the region on the chromatographic strip to which the sample is added or (ii) in between the region to which the sample is added and the region comprising the capture agent such that sample that is added to the test strip flows across the conjugate pad before reaching the region comprising the capture agent.

4. The test strip of claim 2, wherein the chromatographic strip further comprises a sample pad at the region to which the sample is added.

5. The test strip of claim 4, wherein the sample pad allows the sample to be released slowly onto the conjugate pad.

6. The test strip of claim 2, wherein the first detectable marker or the second detectable marker is a fluorophore.

7. The test strip of claim 2, wherein the first detectable marker is a fluorophore that fluoresces upon exposure to light of a first wavelength and the second detectable marker is a fluorophore that fluoresces upon exposure to light of a second wavelength that is different from the first wavelength.

8. The test strip of claim 2, wherein the second agent is a boronic acid or a derivative thereof.

* * * * *